United States Patent
Bresciani

(10) Patent No.: US 10,052,600 B2
(45) Date of Patent: Aug. 21, 2018

(54) ANALYSIS SYSTEM IN ORDER TO OPTIMIZE POWER CONSUMING OF MIXING CARTS ACCORDING TO THE OBJECTIVE PHYSICAL PROPERTIES OF THE UNIFEED

(71) Applicant: DINAMICA GENERALE S.P.A., Poggio Rusco (Mantova) (IT)

(72) Inventor: Matteo Bresciani, Sermide (IT)

(73) Assignee: DINAMICA GENERALE S.P.A., Poggio Rusco (IT)

(*) Notice: Subject to any disclaimer, the term of this patent is extended or adjusted under 35 U.S.C. 154(b) by 287 days.

(21) Appl. No.: 14/929,733

(22) Filed: Nov. 2, 2015

(65) Prior Publication Data

US 2016/0144325 A1 May 26, 2016

(30) Foreign Application Priority Data

Nov. 26, 2014 (EP) .................................. 14195025

(51) Int. Cl.
*A23K 50/00* (2016.01)
*A23K 50/10* (2016.01)
(Continued)

(52) U.S. Cl.
CPC ........ *B01F 15/00259* (2013.01); *A01K 5/001* (2013.01); *A23K 50/00* (2016.05); *A23K 50/10* (2016.05); *A23N 17/007* (2013.01); *B01F 15/00207* (2013.01); *B01F 15/00214* (2013.01); *B01F 15/00253* (2013.01); *B01F 15/00331* (2013.01); *G01N 21/359* (2013.01); *G01N 21/3563* (2013.01)

(58) Field of Classification Search
CPC ........ A01K 5/001; A23K 50/00; A23K 50/10; A23N 17/007; B01F 15/00207; B01F 15/00214; B01F 15/00253; B01F 15/00259; B01F 15/00331; G01N 21/3563; G01N 21/359
See application file for complete search history.

(56) References Cited

U.S. PATENT DOCUMENTS 5,311,290 A * 5/1994 Olson ................ G01N 15/1404
348/142
5,527,107 A * 6/1996 Weibel ...................... B01F 3/18
366/141

(Continued)

FOREIGN PATENT DOCUMENTS

DE 20 2010 005 053 U1 8/2011
DE 10 2010 033 886 A1 2/2012
(Continued)

*Primary Examiner* — Tony G Soohoo
(74) *Attorney, Agent, or Firm* — Pearne & Gordon LLP

(57) ABSTRACT

A system for analyzing feed mixtures, which comprises: a mixing apparatus suitable for containing a plurality of feeds and comprising a mixing means suitable for mixing said plurality of feeds so as to define a feed mixture; a sensing means suitable for acquiring chemical and/or physical parameters of the feed mixture; and a processing unit connected to the sensing means.
The sensing means comprises at least an image acquisition device and the processing unit is configured to determine the degree of homogeneity of the feed mixture and/or configured to determine the length of the fibers included in the mixture.

13 Claims, 1 Drawing Sheet

(51) Int. Cl.
*A01K 5/00* (2006.01)
*A23N 17/00* (2006.01)
*B01F 15/00* (2006.01)
*G01N 21/3563* (2014.01)
*G01N 21/359* (2014.01)

(56) References Cited

U.S. PATENT DOCUMENTS

| | | | | |
|---|---|---|---|---|
| 5,595,696 A * | 1/1997 | Schlarb | ............... | B29B 9/06 264/118 |
| 5,605,841 A * | 2/1997 | Johnsen | ............... | G01N 1/20 250/339.11 |
| 5,786,894 A * | 7/1998 | Shields | ............... | G01N 1/38 250/574 |
| 5,918,977 A * | 7/1999 | Borggaard | ............... | G01N 15/02 366/140 |
| 6,114,699 A * | 9/2000 | Barton | ............... | G01N 21/3563 250/339.09 |
| 6,155,103 A * | 12/2000 | Diekhans | ............... | G01N 1/2035 460/114 |
| 6,517,230 B1 * | 2/2003 | Afnan | ............... | B01F 7/00908 366/142 |
| 7,174,672 B2 | 2/2007 | Beck | ............... | A23K 10/30 47/58.1 FV |
| 7,765,882 B2 * | 8/2010 | Greten | ............... | G01N 1/20 366/131 |
| 7,929,140 B2 * | 4/2011 | Zambuto | ............... | G01J 3/02 356/300 |
| 8,608,368 B2 * | 12/2013 | Bresciani | ............... | A01K 5/00 119/51.01 |
| 8,753,871 B2 * | 6/2014 | West | ............... | C12M 41/48 366/102 |
| 8,949,035 B2 * | 2/2015 | Weakley | ............... | A23K 1/001 702/19 |
| 8,967,851 B1 * | 3/2015 | Kemeny | ............... | B01F 7/00908 366/142 |
| 9,182,765 B2 * | 11/2015 | Ghiraldi | ............... | G05D 11/131 |
| 9,697,483 B2 * | 7/2017 | Dlott | ............... | G06Q 10/063 |
| 2002/0136089 A1 * | 9/2002 | Folestad | ............... | B01F 7/302 366/287 |
| 2004/0012781 A1 * | 1/2004 | Gehrlein | ............... | G01N 21/3563 356/328 |
| 2004/0019462 A1 * | 1/2004 | Gehrlein | ............... | B01F 3/02 702/188 |
| 2004/0100860 A1 * | 5/2004 | Wilmer | ............... | B01F 3/0092 366/136 |
| 2005/0000457 A1 * | 1/2005 | Beck | ............... | A23K 10/30 119/51.02 |
| 2005/0214440 A1 * | 9/2005 | Aberle | ............... | A23J 3/04 426/656 |
| 2006/0080041 A1 * | 4/2006 | Anderson | ............... | B01F 13/1055 702/19 |
| 2006/0138709 A1 * | 6/2006 | Mbachu | ............... | C04B 26/02 264/406 |
| 2006/0255196 A1 * | 11/2006 | Rousseau | ............... | A01F 29/005 241/101.761 |
| 2007/0043471 A1 | 2/2007 | Anderson et al. | | |
| 2007/0043472 A1 | 2/2007 | Anderson et al. | | |
| 2007/0043473 A1 | 2/2007 | Anderson et al. | | |
| 2007/0106425 A1 | 5/2007 | Anderson et al. | | |
| 2007/0251596 A1 * | 11/2007 | Scherzer | ............... | B01F 3/18 141/2 |
| 2008/0066883 A1 * | 3/2008 | Ring | ............... | D21C 7/12 162/198 |
| 2008/0279038 A1 * | 11/2008 | Bellafiore | ............... | G05D 11/139 366/152.4 |
| 2009/0037139 A1 * | 2/2009 | Rust | ............... | G01B 11/024 702/158 |
| 2009/0056162 A1 * | 3/2009 | McMahon, Jr. | ............... | F26B 17/12 34/511 |
| 2009/0298149 A1 * | 12/2009 | Wang | ............... | C07G 1/00 435/165 |
| 2010/0054077 A1 * | 3/2010 | Qvarfort | ............... | B01F 15/00207 366/142 |
| 2010/0287826 A1 * | 11/2010 | Hoffman | ............... | C10L 5/363 44/605 |
| 2011/0064865 A1 * | 3/2011 | McCurdy | ............... | A01K 5/002 426/623 |
| 2011/0261641 A1 * | 10/2011 | Barbi | ............... | A23N 17/007 366/141 |
| 2011/0320033 A1 * | 12/2011 | Bresciani | ............... | A01K 5/00 700/213 |
| 2012/0217192 A1 * | 8/2012 | Blank | ............... | B01D 15/166 210/143 |
| 2012/0287745 A1 * | 11/2012 | Ghiraldi | ............... | G05D 11/131 366/152.1 |
| 2013/0280508 A1 * | 10/2013 | Heinzman | ............... | C08L 3/02 428/219 |
| 2016/0144325 A1 * | 5/2016 | Bresciani | ............... | A23N 17/007 366/279 |

FOREIGN PATENT DOCUMENTS

| | | |
|---|---|---|
| EP | 2 011 390 A1 | 1/2009 |
| EP | 2 377 392 A1 | 10/2011 |
| EP | 2 489 258 A1 | 8/2012 |

* cited by examiner

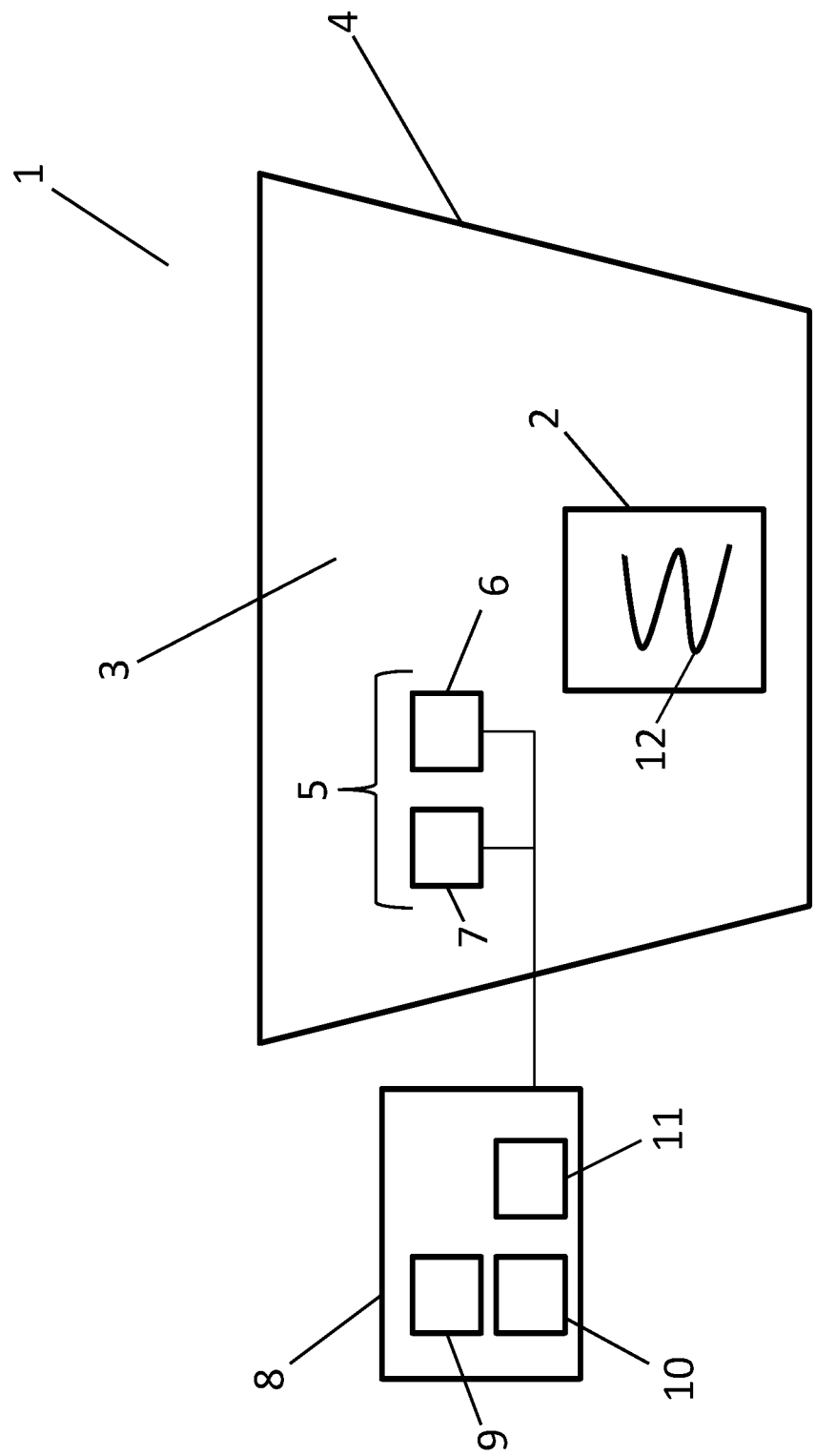

ANALYSIS SYSTEM IN ORDER TO OPTIMIZE POWER CONSUMING OF MIXING CARTS ACCORDING TO THE OBJECTIVE PHYSICAL PROPERTIES OF THE UNIFEED

BACKGROUND

Field of the Invention

The present invention relates to a system for analyzing feed mixtures for zootechnical use.

Description of Related Art

It is well known that the diet and feeding behaviour of livestock decisively influence the quality and yield of zootechnical production.

For example, in the case of dairy cattle farming, the balancing of the diet and method of feeding rations determine productivity and milk quality, as well as animal health and well-being.

For this reason, the diet of livestock and the rationing methods are normally prescribed by a nutritionist.

In modern livestock farming, a feeding technique based on a "single meal", known in jargon as Unifeed (from "unique feed") or also TMR ("Total Mixed Ration") has taken hold.

Unifeed is a homogeneous, balanced mixture of all components of the daily diet.

This mixture is preferably provided to animals in the form of multiple rations distributed over the day.

In the case of dairy cattle, numerous scientific studies have demonstrated that the respective ruminal ecosystem, whose stability determines productivity and milk quality, is favourably influenced by the fact of providing the animals with a large number of meals per day.

In the Unifeed mixture, all of the individual feedstuffs are weighed in such a way as to produce a weighted ration corresponding to the needs of a homogeneous group of animals, i.e. a class of animals having the same nutritional requirements.

In fact, based on the conditions, age, days elapsing since parturition, number of parturitions and function of the animals, the recipe of the mixture will change; for example, a pregnant cow has dietary requirements differing from those of a non-pregnant cow, just as a cow close to parturition has requirements which differ from those of a cow in the early weeks of gestation.

The Applicant has filed a number of patent documents which protect systems and methods for controlling and/or correcting feed rations in order to optimize the nutritional values included in the rations themselves.

In this regard, see, for example, European patents no. EP2011390 and no. EP2489258 or European patent application no. EP2377392.

In detail, such optimization is determined by whether the mixture provided to the animal actually corresponds to the theoretical recipe established by the nutritionist.

As is well known, the dosage of each feedstuff, or ingredient, of the mixture and the preparation of the rations are achieved by means of a mixer wagon, into which the feedstuffs are loaded based on the pre-established recipe.

The recipe prescribes the weights of the different feedstuffs and also the respective order of loading into the mixer wagon.

The mixer wagon comprises within it one or more mixing screws endowed with cutting edges that shred the mixture and render it uniform.

Field experience has demonstrated that, in addition to the correct loading of the various ingredients in optimal amounts, the degree of homogeneity of the mixture and length of the fibres present in the mixture itself are among the factors which contribute to the final effectiveness of the feeding methods discussed above.

In fact, the more homogeneous the mixture is, the more constant and uniform the distributed mixed feed will be in the various points of the feed trough, preventing animals of the same group from being fed in a different manner.

Moreover, the more homogeneous and finely chopped a mixture is, the less the animals will be able to select the most palatable feedstuffs, leaving the ones rich in fibre but less appealing on the ground; this prevents the effort of creating and following the recipe from being undermined.

It should be noted that the presence of fibres of considerable length in an animal's diet is very important in order to improve rumination and reduce the probability of having metabolic imbalances.

To date, control over the optimization of the parameters discussed above has been limited to the mixing time or the number of rotations of the screws in the mixer wagon, based on the fact that the degree of homogeneity of the mixture is proportional.

A long period of mixing, especially if it is carried out at a high screw rotation speed, results in a considerable energy consumption of the wagon and can determine an excessive degree of shredding of the fibres, which become short and split, strongly reducing the benefit thereof.

On the other hand, short, slow mixing produces a scarcely homogeneous mixture.

At present, the mixing period and speed are established before every mixing operation based on empirical correlations between the degree of homogeneity and of shredding of different mixtures and the respective times and/or number of rotations of the mixing screws used.

Such correlations are necessarily very approximate given that they are based on measurements that cannot take into account the intrinsic variability of feedstuffs originating from different crops, different cuttings on the same field or simply crops gathered from different points of the same field, just as they cannot take into account the variability in the sharpening of the cutting edges of the screws or still other factors.

SUMMARY

In this context, the technical task at the basis of the present invention is to propose a system for analyzing feed mixtures which makes it possible to optimize the energy consumption of the mixing devices used in the livestock sector.

Within the scope of this task, one object of the invention is to provide a system for analyzing feed mixtures which enables homogeneous mixtures to be obtained without damaging or excessively shortening the fibres contained therein.

The specified task and object are achieved by a system for analyzing feed mixtures made in accordance with claim 1.

Additional features and advantages of the present invention will become more apparent from the approximate, and hence non-limiting, description of a preferred but non-exclusive embodiment of the system of analysis of the invention, as described hereunder.

BRIEF DESCRIPTION OF THE DRAWINGS

FIG. 1 is a schematic representation of an apparatus suitable for mixing a plurality of feedstuffs.

DETAILED DESCRIPTION OF PREFERRED EMBODIMENTS

As shown in FIG. 1, the proposed system of analysis comprises first of all a mixing apparatus (1) suitable for containing a plurality of feedstuffs and comprising mixing means (2) suitable for mixing the plurality of feedstuffs, so as to define a feed mixture.

The feedstuffs are the ingredients, or doses, of the feed recipe for zootechnical use, which was broadly discussed in the description of the prior art.

The mixing apparatus (1) comprises a mixing chamber (3) for containing the feedstuffs during mixing.

The mixing means (2) can be of the type suitable for mixing and shredding the feedstuffs.

Preferably, the mixing apparatus (1) is a mixer wagon (4) and the mixing means (2) comprises one or more rotating screws (12) endowed with a cutting edge and enclosed in the aforesaid chamber (3).

In detail, said mixing chamber (3) is obtained in the body of the wagon (4). The system can include motorized members for driving the screws (12) in rotation and a control unit mounted on the wagon for controlling their operation and rotation speed.

The proposed system comprises a sensing means (5), preferably located in the mixing chamber (3) and suitable for acquiring chemical and/or physical parameters of the aforesaid feed mixture.

In practical terms, the sensing means (5) are configured to acquire the aforesaid parameters whilst the feedstuffs are being mixed by the mixing means (2).

Physical parameters can be understood as conformational or metrical characteristics of the mixture; in detail, the configuration of the mixture as derived from the observation of its appearance is a physical parameter according to the invention.

Chemical parameters are to be understood as characteristics related to the composition of the mixture, both in terms of the type of ingredients and in terms of the chemical composition or chemical properties thereof.

According to an important aspect of the invention, the sensing means (5) comprises an image acquisition device (6), preferably located in said mixing chamber.

In this case, the physical parameter that the acquisition device (6) is capable of collecting is the visual appearance of the mixture, obtained by the recording of a sequence of images, preferably digital ones, in particular frames, by the device itself.

The acquisition device (6) can be endowed with memory means suitable for storing the images acquired in sequence.

The acquisition device is preferably a camera; however, another acquisition means can be used provided that it is suited to the purpose. Optionally, the sensing means can also comprise an NIR ("Near Infrared Radiation) device (7) suitable for determining the spectrum of electromagnet radiation reflected by the feedstuffs.

This aspect will be further discussed in a paragraph below.

Advantageously, the invention comprises a processing unit (8) connected to the sensing means (5) and configured to determine the degree of homogeneity of the feed mixture and/or configured to determine the length of the fibres included in the mixture.

More precisely, the fibre length that is measured by the proposed system can be an average length.

In even greater detail, the processing unit (8) is configured to analyze the acquired images, which show the appearance of the mixture, and to measure the degree of homogeneity and/or length of the fibres of the mixture.

It should be noted that the system can be used to measure only homogeneity or only the fibre length or both, simultaneously or separately. In the preferred embodiment of the invention, the processing unit (8) is configured to regulate, on a real-time basis, instant by instant, the operation of the mixing means (2) based on the degree of homogeneity and/or fibre length.

More precisely, the system automatically regulates the activation and speed of the mixing means (2), for example of the aforesaid screws (12), based on the measurements made on the mixture while it is being mixed. If the mixing means (2) comprises the aforesaid control unit, the processing unit (8) will be configured to pilot the control unit in such a way that it regulates the duration and speed of the mixing.

The processing unit (8) can be located externally to the mixing apparatus (1) or else be mounted on the same, possibly integrated or connected with a central unit already present in the apparatus (1).

If the processing unit (8) is external to the wagon (4), or another mixing apparatus (1), it can communicate with the aforesaid control unit and/or central unit by means of wireless systems, for example of the radiofrequency type, or by using storage media or cables or the like.

It should be noted that the processing unit (8) is presented hereunder as divided into distinct functional modules (memory modules or operating modules) for the purpose of describing the functions thereof in a clear and complete manner.

Practically, the processing unit (8) can consist in a single electronic device, duly programmed to perform the functions described, and the various modules can correspond to hardware and/or routine software entities belonging to the programmed device.

Alternatively, or in addition, these functions can be performed by a plurality of electronic devices over which the aforesaid functional modules can be distributed.

In the preferred embodiment of the invention, the processing unit (8) comprises a memory module (9) configured to store a target degree of homogeneity and/or a target fibre length defined by the user; moreover, the memory module (9) can also be capable of recording the recipe understood as a sequence of ingredients and, for each ingredient, the target weight together with characterizing chemical parameters.

In this case, the processing unit (8) is advantageously configured to deactivate the mixing means (2) when the degree of homogeneity of the feed mixture is at least equal to said target degree of homogeneity and/or when the length of the fibres in the feed mixture is substantially equal to the target length.

The processing unit (8) can comprise a first analysis module (10) configured to compare a plurality of the images of the sequence collected by the aforesaid acquisition device (6).

In this case, the first analysis module (10) is preferably configured to calculate the degree of homogeneity of the mixture based on the similarity between successive images included in the sequence.

More precisely, the first analysis module (10) is capable of performing an analysis of the images collected by the acquisition device (6) using imaging techniques, which may also be of a known type, but not in combination with the remaining features of the invention.

In detail, the first module (10) measures the differences among the various images considered, estimating their similarities with the methods explained below.

In this case, the aforesaid target degree of homogeneity recorded in the memory module (9) either coincides with or is correlated to the degree of similarity among the images.

When the first analysis module (10) verifies that the degree of similarity among the images acquired over time is substantially equal to the target, the processing unit (8) can stop the mixing means (2).

In other words, as the mixing process proceeds, the degree of homogeneity of the mixture increases and the distance between successive images decreases until reaching a higher threshold value which represents an acceptable level of homogeneity.

The similarity between successive images can be determined by the first analysis module (10) by measuring a reciprocal topological distance which, by way of non-exhaustive example, is the Mahalanobis distance.

In the preferred embodiment of the invention, the processing unit (8) comprises a second analysis module (11) configured to identify, within the images collected by the acquisition device (6), the fibres included in the mixture and configured to measure the fibre length.

As mentioned above, the second analysis module (11) is preferably capable of measuring the average length of the fibres.

The second module (11) can be configured to identify filiform objects within said images, in such a way as to identify the fibres which have, precisely, a filiform appearance.

In order to identify the fibres within the images representing the mixture and measure their length, the second module (11) also uses imaging techniques.

As already mentioned, the system can include an NIR device (7) as well as an image acquisition device (6).

The NIR device (7) is capable of acquiring parameters of a chemical type and can be used to measure the uniformity of distribution of such parameters within the mixture by reading different physical samples in successive instants, thus determining the homogeneity of the mixture.

The NIR device (7) can be used as an aid to the image acquisition device (6) in measuring homogeneity, or else it can be the component intended to measure homogeneity whilst the acquisition device is intended to measure the fibre length.

The operation of the proposed system is described here below.

The user sets the target values in the memory module (9), for example via a usual user interface, or else sets the values on a personal computer or server or smartphone or tablet and sends them via a wireless communication means (Wi-Fi, Bluetooth, . . . ) or records them in the memory module (9) by means of a portable storage device (USB . . . ). These values, as said previously, can vary based on the feed recipe and can thus be different for homogeneous groups of animals.

In detail, for some livestock needs it is possible that the only relevant target value is a certain degree of homogeneity of the mixture, just as for other needs the only relevant target value might be a minimum fibre length.

In general, the user can set both a target degree of homogeneity and a target degree of length, for example based on an optimization between the two values established by the nutritionist or by studies in the field.

Afterwards, the feedstuffs will be loaded into the mixer wagon (4), based on the specifications of the recipe.

At this point, the screws (12) start mixing the feedstuffs, based on a programmed speed, so as to make a mixture thereof.

The camera, or other acquisition device (6), and optionally the NIR device (7), picks up the characteristics of the mixture while it is being formed.

The analysis modules (10, 11) of the processing unit measure the values of homogeneity and fibre length, according to the above-described methods.

Given that the measurement is real-time, it has the undoubted advantage of enabling feedback control to be performed based on the actual measurement of the control parameters, which is not subject to errors due to the intrinsic variability of the feedstuffs, the different speed of the screws (12), or the different degree of sharpness of the screws (12) or other variables.

Therefore, the proposed system is much more reliable compared to the prior art and does not require complex and approximate estimates to be made a posteriori.

Furthermore, once the targets are reached, the processing unit (8) immediately stops the screws (12), ensuring an optimal result in terms of mixing and avoiding wastes of energy.

In fact, with the use of the invention, it is no longer necessary to set a mixing time capable of mixing correctly even in the worst case in order to ensure good homogeneity, since the latter is directly sensed instant by instant while the wagon (4) is carrying out the mixing process.

Moreover, in this manner the highly important fibres contained in the mixture will not be shredded excessively, thereby limiting the effectiveness thereof in the rumination of the animals, and the limits of the prior art are overcome.

Therefore, at each mixing, the targets to be reached can be set by the user based on the livestock feed requirements.

If the objectives are the same for different mixtures, a constant quality of the desired mixture can be secured.

If, in contrast, the intended use of the mixture changes, the system makes it possible to satisfy all of the feed requirements that different animals can have under different conditions.

Finally, it should be noted that the proposed system can also include weight sensing devices and measuring devices located in the wagon (4) and provided to optimize the composition of the recipe.

In this case, the processing unit (8) will be configured to manage the sensors and devices in accordance with the purpose of the analysis and correction of the mixture.

As regards the latter aspect, the characteristics of the sensors and devices as described in the previous applications of the Applicant are to be considered incorporated by reference into the present disclosure.

The invention claimed is:

1. An apparatus for analyzing feed mixtures, comprising: at least a mixing apparatus suitable for containing a plurality of feeds and comprising mixing means suitable for mixing said plurality of feeds so as to define a feed mixture; a sensing means suitable for acquiring chemical and physical parameters of said feed mixture; and at least a processing unit connected to said sensing means; wherein the sensing means comprises at least an image acquisition device which is a camera provided to collect images of the feed mixture; said processing unit being configured to determine a degree of homogeneity of the feed mixture and a length of the fibres included in the feed mixture.

2. The apparatus according to claim 1, wherein the processing unit is configured to regulate the operation of the mixing means based on said degree of homogeneity and/or said fibre length.

3. The apparatus according to claim 2, wherein the processing unit comprises at least a memory module configured to store a target degree of homogeneity and/or a target fibre length, wherein said processing unit is configured to stop the mixing means when the degree of homogeneity of the feed mixture is greater than or equal to said target degree of homogeneity and/or the length of said fibre in the feed mixture is less than or equal to said target length.

4. The apparatus according to claim 1, wherein said processing unit comprises a first analysis module configured to compare a plurality of images collected by said acquisition device.

5. The apparatus according to claim 4, wherein said first analysis module is configured to calculate the degree of homogeneity of the feed mixture based on the similarities between successive images.

6. The apparatus according to claim 5, wherein the first module is configured to determine said similarity between successive images by measuring a reciprocal topological distance.

7. The apparatus according to claim 6, wherein the first module is configured to measure the Mahalanobis distance between successive images.

8. The apparatus according to claim 1, wherein said processing unit comprises a second analysis module configured to identify, within the images collected by the acquisition device, the fibres included in the feed mixture and configured to measure the length of said fibres.

9. The apparatus according to claim 8, wherein said second module is configured to identify filiform objects within said images.

10. The apparatus according to claim 1, wherein said mixing apparatus is a mixer wagon and wherein the mixing means comprises at least a rotating screw provided with at least one cutting edge.

11. The apparatus according to claim 1, wherein said sensing means comprises a near infrared radiation device suitable for determining the spectrum of the electromagnetic radiation reflected and/or absorbed by said feed.

12. The apparatus according to claim 1, wherein the mixing apparatus comprises a mixing chamber for containing said feed and wherein the sensing means is disposed in said chamber.

13. An apparatus for analyzing feed mixtures, comprising: a mixing apparatus comprising one or more mixing screws; a camera to capture an image of a feed mixture in the mixing apparatus; a processing unit to receive the image from the camera; wherein the processing unit is configured to determine a degree of homogeneity of the feed mixture and a length of the fibres in the feed mixture based on the image received from the camera.

* * * * *